US00PP20433P2

(12) United States Plant Patent
Probst

(10) Patent No.: US PP20,433 P2
(45) Date of Patent: Oct. 20, 2009

(54) ***GENTIANA* PLANT NAMED 'TRUE BLUE'**

(50) Latin Name: ***Gentiana* hybrid**
Varietal Denomination: True Blue

(76) Inventor: Darrell R. Probst, 63 Williamsville Rd., Hubbardston, MA (US) 01452-1315

( * ) Notice: Subject to any disclaimer, the term of this patent is extended or adjusted under 35 U.S.C. 154(b) by 0 days.

(21) Appl. No.: 12/286,713

(22) Filed: Oct. 1, 2008

(51) Int. Cl.
*A01H 5/00* (2006.01)

(52) U.S. Cl. ..... Plt./433
(58) Field of Classification Search ..... Plt./263, Plt./433
See application file for complete search history.

*Primary Examiner*—Susan B McCormick Ewoldt
(74) *Attorney, Agent, or Firm*—Penny J. Aguirre

(57) ABSTRACT

A new cultivar of *Gentiana* named 'True Blue', characterized by its sturdy, well-branched stems that are held upright, its ease of cultivation in ordinary garden soils, its semi-glossy leaves, its large blue flowers that open and are rich bright blue in color on both the inner and outer petal surfaces, and its hardiness in U.S.D.A. Zones 4 to 8.

2 Drawing Sheets

Figure 1:
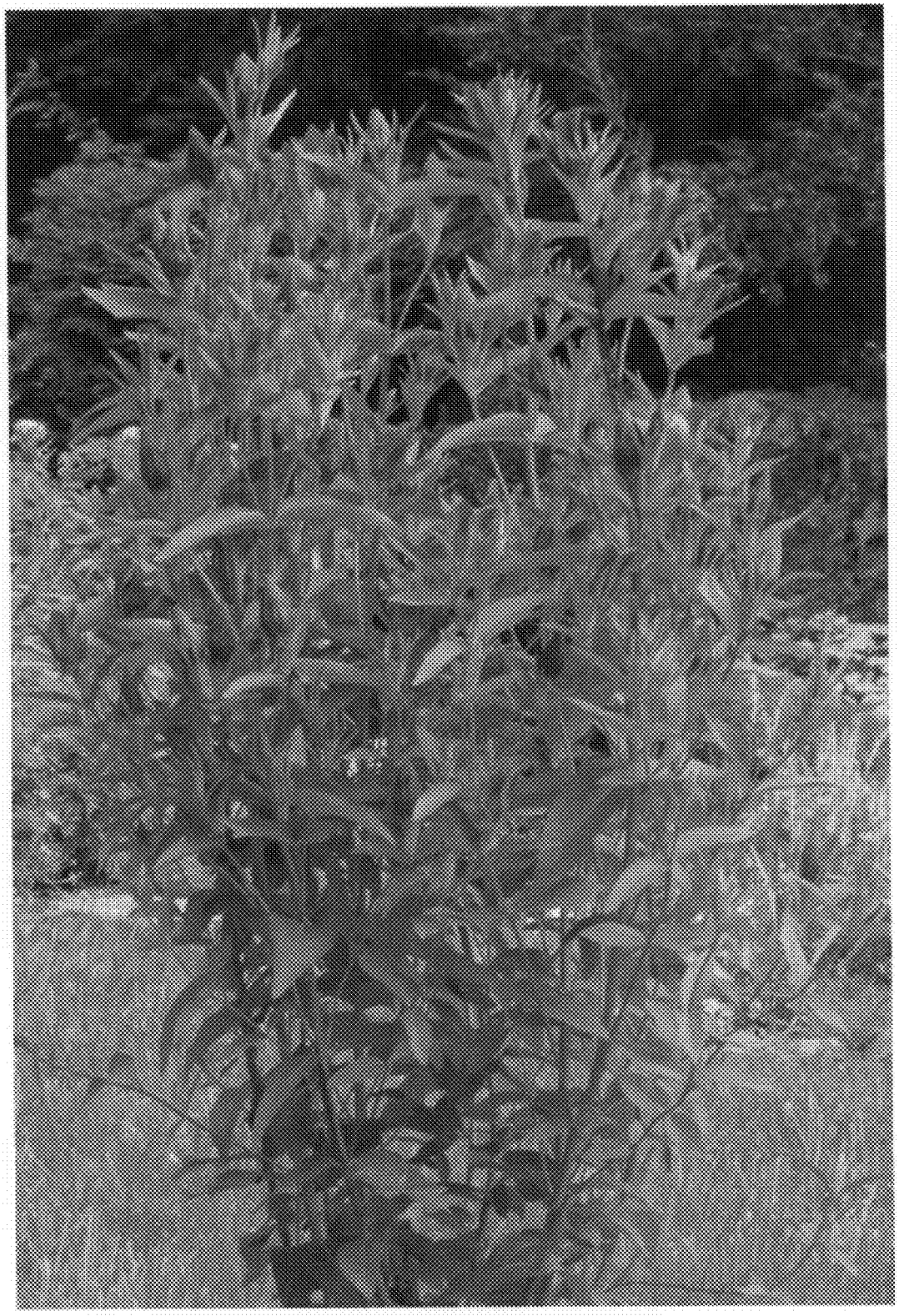

Botanical classification: *Gentiana* hybrid.
Varietal denomination: 'True Blue'.

BACKGROUND OF THE INVENTION

The present invention relates to a new and distinct cultivar of *Gentiana* of hybrid origin and will be referred to hereafter by its cultivar name, 'True Blue'. 'True Blue' represents a new Gentian, an herbaceous perennial grown for landscape use.

The new Invention arose from an ongoing controlled breeding program in Hubbardston, Mass. The objective of the breeding program is to develop hybrid cultivars of *Gentiana* with unique and superior garden attributes. In particular, to develop plants that are well branched with sturdy and upright plant habits, that exhibit a long season of bloom, and that exhibit flowers that open and are true blue in color on both the inner and outer petal surfaces.

The Inventor made a controlled cross in 2001 in his test garden in Hubbardston, Mass. between an unnamed plant of a hybrid of *Gentiana makinoi* as the female parent and an unnamed plant of unknown botanical origin as the male parent (possibly a species or hybrid related to *Gentiana scabra*). Neither parent is patented. 'True Blue' was selected in August 2004 as a single unique plant amongst the resulting seedlings.

Asexual reproduction of the new cultivar was first accomplished by division in Hubbardston, Mass. in 2006. It has been determined by propagation both by division, stem cuttings and tissue culture that the characteristics of the new cultivar are stable and are reproduced true to type in successive generations.

SUMMARY OF THE INVENTION

The following traits have been repeatedly observed and represent the characteristics of the new cultivar after observing plants grown outdoors in a field for four years in Hubbardston, Mass. These attributes in combination distinguish 'True Blue' from all other cultivars of *Gentiana* known to the Inventor.

1. 'True Blue' exhibits sturdy upright stems.
2. 'True Blue' is well branched.

3. 'True Blue' has a long bloom season; blooming from mid July to mid September.
4. 'True Blue' grows in ordinary garden soil with sufficient moisture.
5. 'True Blue' has leaves with a semi-glossy surface.
6. 'True Blue' exhibits large flowers that open and are bright blue in color on both the inner and outer surface of the petals.
7. 'True Blue' is hardy in U.S.D.A. Zones 4 to 8.

'True Blue' differs from its female parent in that the female parent is taller in height, has flowers that open just slightly, has leaves with a dull surface, and blooms for a shorter period of time (about one month). The male parent differs from 'True Blue' in being shorter in height, in having sprawling stems, and in having flowers with an outer petal surface that is dull gray-blue in color. 'True Blue' can be compared to *Gentiana makinoi* 'Marsha' (U.S. Plant Pat. No. 16,562). 'Marsha' is similar to 'True Blue' in its easy of growing in ordinary garden soils and in having upright stems, however 'True Blue' differs from 'Marsha' in having better branching, glossier leaves, a longer bloom period, and in having flowers that are more open and richer deeper blue in color.

BRIEF DESCRIPTION OF THE PHOTOGRAPHS

The plants and plant parts in the photographs were taken of a four year-old plant of 'True Blue' as grown outdoors in a test garden in Hubbardston, Mass.

The photograph in FIG. 1 provides an overall view of 'True Blue' in bloom.

Figure 2:
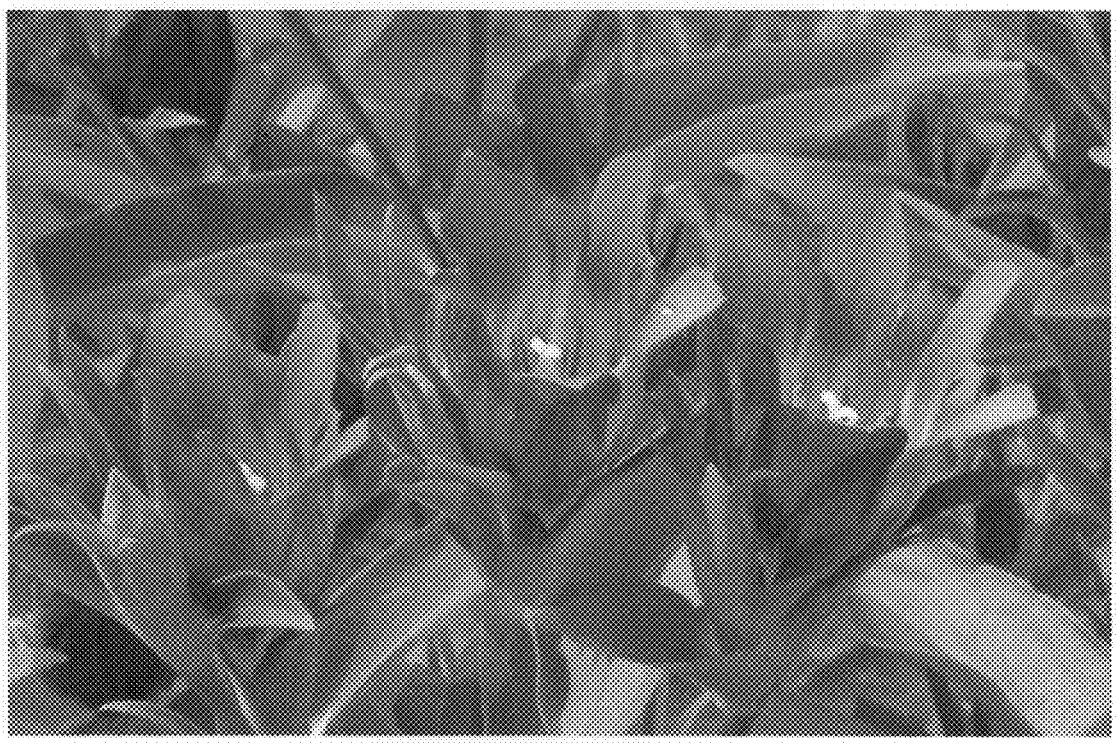

The photograph in FIG. 2 is a close-up view of the flowers of 'True Blue'.

The Colors in the photograph may differ slightly from the color values cited in the detailed botanical description, which accurately describe the colors of the new *Gentiana*.

DETAILED BOTANICAL DESCRIPTION

The following is a detailed description of 4 year-old plants of the new cultivar as grown outdoors in full sun in Hubbardston, Mass. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—Continuously from mid July to mid September in Massachusetts.

*Plant type.*—Herbaceous perennial.

*Plant habit.*—Clump-forming, upright, and well-branched.

*Height and spread.*—Reaches 46 to 76 cm in height (18 to 30 inches) and an average of 46 cm in spread (18 inches).

*Hardiness.*—U.S.D.A. Zones 4 to 8.

*Culture.*—Grows well in ordinary garden soils with sufficient moisture.

*Diseases.*—No unique susceptibility or resistance to diseases has been observed.

*Root description.*—Fine.

Growth and propagation:

*Propagation.*—Stem cuttings, division, and tissue culture.

*Growth rate.*—Moderately vigorous.

Stem description:

*Stem shape.*—Nearly round.

*Stem color.*—Blend of 146B and 146C.

*Stem size.*—Average of 60 cm in height, average of 1.5 cm in diameter.

*Stem surface.*—Glabrous and satiny.

*Stem aspect.*—Sturdy, held strongly upright.

*Internode length.*—Average of 5 cm.

*Branching habit.*—Well branched with flowering branches emerging from nodes in an opposite arrangement, an average of 9 lateral branches per main stem 57 cm in length.

Foliage description:

*Leaf shape.*—Lanceolate.

*Leaf division.*—Simple.

*Leaf base.*—Cuneate.

*Leaf apex.*—Narrowly acute.

*Leaf venation.*—Tri-nerved, only mid ribs are conspicuous, 144C in color on upper surface and 147C on lower surface.

*Leaf margins.*—Entire.

*Leaf attachment.*—Sessile.

*Leaf arrangement.*—Opposite.

*Leaf aspect.*—Held nearly horizontal to stem and concave in respect to the mid rib on the upper surface,

*Leaf surface.*—Upper and lower surface; very finely puberulent on both surfaces with upper surface appearing semi-glossy and lower surface appearing glaucous, leaves become slightly leathery when mature.

*Leaf color.*—New leaves upper surface; blend of 137A and 144A, new leaves lower surface; blend of 146B and 138B, mature leaves upper surface; blend of 137B and N137A with a small area of 145B to 145C at base, mature leaves lower surface; blend of 146B and 138B.

*Leaf number.*—An average of 60 pairs of leaves on a stem 60 cm in length (including laterals).

*Leaf size.*—Up to 8 cm in length and 3.5 cm in width when mature.

Flower description:

*Inflorescence type.*—Solitary sessile flowers at terminals of each lateral branch with one to two flowers arising on peduncles from terminals and solitary flowers on peduncles arising from axillary nodes of lateral branches.

*Flower type.*—Campanulate, fully open with sun exposure.

*Flower fragrance.*—None.

*Flower lastingness.*—Average of 10 days on plant, average of 14 days as a cut flower, persistent.

*Flower bud description.*—Oblong to narrowly elliptic in shape, average of 9 mm in diameter and 3.3 cm in length, color of petal portion; blend of 94B and 147A to 147B color of sepal portion is 145B with veins 144A on fused base with free portion same as leaf colors.

*Flower quantity.*—Average of 28 per stem.

*Flower aspect.*—Held upright to stem.

*Flower size.*—5.6 cm in depth, 2.8 cm in diameter.

*Peduncle description.*—Present on lateral flowers, rarely present on terminal flowers, about 5 cm in length and 2 mm in width, held at an average angle of about 20° relative to stem, 144A to 144B in color with base sometimes suffused with N77A, glabrous surface.

*Petals.*—5, oblong in shape with center triangular areas between oblong portion with acute tips, 80% of lower portion is fused, an average of 5.2 cm in length and 1.5 mm in width with free apex about 1 cm in length and diameter, margin is entire, apex is acute with a tiny cuspidate tip, surface is smooth and slightly glossy in appearance, color of outer surface (opening and fully open); blend of 96A and 96B and suffused with 93A to 93B at edges, blended with 147A in mid portion and a blend of 145B and 145C at base (hidden by calyx), color of inner surface (opening and fully open); apex 93B blending in center region with 96A to 96B, lower region 97D with stripes of 203A, and a blend of 145B to 145C at base, color when fading; blend of 94A, to 94B, 93B, and 147A.

*Calyx.*—Campanulate in form with un-fused portion of sepals spreading, average of 5 cm in length and 6 cm in diameter to edge of spreading sepals and fused portion is up to 1.4 cm in diameter.

*Sepals.*—5, free portion is linear in shape with entire margin and acute apex and base is truncate to fused portion, surface is smooth and dull in appearance, average of 5 cm in length with free portion an average of 3 cm in length and 3.5 mm in width, color of outer surface; free portion a blend of 146B and 138B, fused portion 145B with veins 144A, color of inner surface; free portion a blend of 137B and N137A, fused portion 144D with veins 144C.

Reproductive organs:

*Gynoecium.*—1 Pistil about 3.5 cm in length, stigma is bifid, decurrent and 165A in color, style is about 3.4 cm in length and 6 mm in width, oblanceolate in shape and 145B to 145C, ovary is superior and 145A in color.

*Androcoecium.*—5 stamens about 3 cm in length and up to 3 mm in width, filaments are adnate to petals, about 2 cm in length, 3 mm in width and 145D in color, connectives are about 8 mm in length and N77B in color, anthers are basifixed, about 3 mm in length and 12B in color, pollen is moderate in quantity and about 11C in color.

*Fruit/seed.*—No seed has been observed under the conditions tested.

It is claimed:

1. A new and distinct cultivar of *Gentiana* plant named 'True Blue' as herein illustrated and described.

* * * * *